United States Patent [19]

Gebhart et al.

[11] 4,370,986
[45] Feb. 1, 1983

[54] METHOD AND APPARATUS FOR DETERMINING THE DEPOSITION OF PARTICLES IN THE RESPIRATORY TRACT AND/OR FOR CHECKING THE FUNCTION OF THE RESPIRATORY TRACT

[75] Inventors: Josef Gebhart, Dietzenbach; Gerhard Heigwer, Offenbach; Joachim Heyder, Frankfurt am Main; Willi Stahlhofen, Bad Homburg, all of Fed. Rep. of Germany

[73] Assignee: Gesellschaft fur Strahlen-und Umweltforschung mbH München, Neuherberg, Fed. Rep. of Germany

[21] Appl. No.: 191,821

[22] Filed: Sep. 26, 1980

[30] Foreign Application Priority Data

Sep. 26, 1979 [DE] Fed. Rep. of Germany ....... 2938856

[51] Int. Cl.³ .............................................. A61B 5/00
[52] U.S. Cl. ................................... 128/716; 128/725; 128/665
[58] Field of Search ................................ 128/664–665, 128/718–719, 725, 716

[56] References Cited

U.S. PATENT DOCUMENTS 4,067,320  1/1978  Olsson et al. ...................... 128/719

Primary Examiner—Kyle L. Howell
Assistant Examiner—Francis J. Jaworski
Attorney, Agent, or Firm—Spencer & Kaye

[57] ABSTRACT

A method and apparatus for determining the deposition of particles in the respiratory tract and/or for checking the operating function of the respiratory tract by means of pulses of gases or aerosols injected into a stream of air inhaled by a test patient and by obtaining a measuring signal in each of the inhaled and exhaled streams. The main stream of the inhaled and exhaled air is conducted directly through a band of light (3), and the region of the intersection of the band of light with at least part of the inhaled and exhaled streams is placed in the object plane of an optical image system for a light measuring device. Either the individual pulses generated by the individual particles in the inhaled and exhaled streams or the scattered radiation emanating from the gases and aerosols in these streams is measured to obtain the ratio of the exhaled to the inhaled numbers of particles and/or the concentration profile in the inhaled and exhaled streams.

14 Claims, 5 Drawing Figures

METHOD AND APPARATUS FOR DETERMINING THE DEPOSITION OF PARTICLES IN THE RESPIRATORY TRACT AND/OR FOR CHECKING THE FUNCTION OF THE RESPIRATORY TRACT

BACKGROUND OF THE INVENTION

The present invention relates to a method and apparatus for determining the deposition of particles in the respiratory tract of an individual, and/or for monitoring the function of the respiratory tract, by means of gas or aerosol pulses and measuring signals obtained from both the inhalate and exhalate streams of the individual.

Within the general examination of biological-medical influences of environmental substances, the exposure to contaminants by way of inhalation plays an important part. In this connection, two important partial aspects must be examined.

(a) What proportion of the particulate matter contained in the breathing air is deposited in the human respiratory tract and what are the parameters on which this depends? Such results are important for the initiation of suitable preventive measures.

(b) How can pathological changes in the respiratory tract as a result of prolonged exposure to contaminants be detected in time?

The first studies to examine the deposition of aerosol particles in the lungs employed the filter technique. Separate filter samples are taken from the inhaled and exhaled air of an individual and the particle concentration on the two filters is compared. However, in these processes, uncontrollable particle losses in the collecting and sampling systems may considerably falsify the particle deposition in the lungs as it is to be measured. A significant advance was made when, according to a proposal by B. Altshuler et al., A.M.A. Arch. Ind. Health (1957) Vol. 15, page 293, the concentration in the number of particles in the inhaled and exhaled breathing air was measured in a photometer directly in front of the mouth of the person being examined and was recorded continuously. From the volume curve simultaneously recorded by an expirograph, graphical integration then yielded the ratio of the number (N) of exhaled to inhaled particles, $N_e/N_i$. A subsequent article by J. Heyder et al., "Experimental Studies of the Total Deposition of Aerosol Particles into Human Respiratory Tract", *Aerosol Science* (1973) Vol. 2, pages 191–208 then taught changing the integration to an electronic base by continuously measuring, in addition to the particle concentration c (by photometry), also the volume stream V of the breathing air (by pneumotachography). There then results the following equation for the ratio of exhaled to inhaled number of particles per breath:

$$\frac{N_e}{N_i} = \frac{\int_{|(\tau_e)|} c\, V\, dt}{\int_{|(\tau_i)|} c\, V\, dt} \quad (1)$$

where $t_e$ is the duration of exhalation and $t_i$ is the duration of inhalation. In spite of the continuous recording of the concentration of the aerosol particles in front of the mouth of the test person and automation of the evaluation, the so-called analog method for determining a number of particles N according to equation (1) still has the following inherent drawbacks:

(1) It is limited to monodispersed aerosols. Each background of another, undesirable size fraction contributes to the values obtained from the photometer.

(2) Particles having hygroscopic surface layers attract water in the respiratory tract, and thus change their optical properties. Consequently, the photometer can no longer distinguish between a change in the number concentration c and a change in the scattering properties of the particles.

(3) In order to be able to make a continuous recording, it is necessary to have a relatively high particle concentration.

In addition to the standard clinical methods for performing lung tests with body plethysmographs (lung volume, airway resistance) it has recently become customary to make the patient inhale inert gases or short pulses of such gases and to draw conclusions as to the ventilation behavior of the lungs and thus to possible pathological changes from the wash out curves or the dispersion, respectively, of these gas pulses in the exhalate.

Such methods require continuous measurements of gas concentrations in the breathing air of test patients. In the past, three major physical principles have been used for such measurements:

1. mass spectroscopy;
2. infrared absorption at specific absorption lines of the gases;
3. changes in the thermal resistance in an environmental gas with changed thermal conductivity.

However, all these methods have the drawback that they do not take concentration measurements of the gas directly in the main stream of the breathing air. Rather, a representative sample must continuously be taken thus adversely influencing the time and volumetric resolution of the concentration curve.

SUMMARY OF THE INVENTION

It is therefore the object of the present invention to provide a method and an apparatus with which it is possible to determine with great sensitivity the deposition of particles in the respiratory tract as well as the operational efficiency of the respiratory tract.

This is accomplished by the method according to the invention by directly conducting the main stream of the inhaled and of the exhaled air from a test patient through a band of light; placing the region of the intersection of the band of light with at least part of the inhaled and exhaled streams in the object plane of an optical image system of a light detecting device; and detecting the light radiation produced in the object plane by the inhaled and the exhaled streams to provide a measuring signal. According to one embodiment of the invention the individual light pulses generated by individual aerosol particles in the inhaled and exhaled streams are detected and counted to obtain the ratio of exhaled to inhaled numbers of particles. According to another embodiment of the invention, the scattered radiation emanating from the gases and aerosol in the inhaled and exhaled streams is detected and measured to obtain the concentration profiles of the constituents of the inhaled and exhaled streams.

The apparatus according to the invention includes an arrangement for determining the deposition of particles in the respiratory tract and/or for checking the operating function of the respiratory tract of a test patient by measuring light radiation from gases or aerosols in the inhaled and exhaled air streams of the test patient, which arrangement comprises: a housing; channel means for conducting a stream of inhaled or exhaled air through the housing with this channel means having an orifice at one end for the inhaled and exhaled air of the test patient and a flow meter for the inhaled and exhaled air; means for conducting a band of light through the housing in a direction transverse to the direction of the channel means and intersecting same within the housing; and a light measuring means, including an optical observation system which is mounted on the housing such that its object plane coincides with the plane of intersection of the band of light and the channel means.

According to further features of the invention, the flow meter includes means for determining the direction of the stream of inhaled or exhaled air in the channel means, and means are provided, and connected to the channel means so that the housing is between same and the orifice, for selectively injecting a pulse of a gas or aerosol into the air stream to be inhaled by the test patient. Preferably this injection means includes a pulse chamber filled under pressure with a gas or aerosol, a normally closed valve connected between the pulse chamber and the channel means, and means for opening the valve at a desired time, whereby opening of the valve at a desired time during the inhalation of the air stream by the test patient will cause the gas or aerosol in the test chamber to expand and enter the channel means for inhalation by the test patient.

DETAILED DESCRIPTION OF THE PREFERRED EMBODIMENTS

According to the basic concept of the present invention the measurements to determine the numbers of inhaled and exhaled particles and/or the concentration profiles of gases and aerosols in the inhaled and exhaled air streams is carried out directly on the main stream of the inhaled and exhaled air streams and a special arrangement or photometer is provided for this purpose.

The present invention therefore provides a special photometer with high sensitivity which counts the particles directly in the main stream of the breathing air in that the scattered light pulses emanating from the individual particles are recorded and additionally the amplitude of the pulses provides a conclusion as to the size of the particles. Moreover, the sensitivity of the photometer has been increased to such an extent that a distinction can be made between the Rayleigh scattering of various gases. For gases whose scattering properties differ from air, concentration measurements can thus be made directly in the main stream of the breathing air.

The determination of the number of inhaled and exhaled particles by means of direct counts in the main stream of the breathing air as provided by the present invention has, for example, the following advantages compared to the prior art indirect methods:

1—by separately storing the size spectra of inhaled and exhaled particles, it can be determined whether and to what extent hygroscopic particles have attached themselves to the respiratory tract;

2—particle sizes outside of a given size range can be excluded from the count so that it becomes possible to determine, with the aid of polydispersed aerosols, the probability of deposition of narrowly defined size fractions in the human respiratory tract; and 3—very small particle concentrations of less than $10^T/cm^3$ (where T means particles) will suffice for the counting method so that the lungs of a test patient will practically not be stressed at all.

This digital counting method according to the invention provides the ratio of exhaled (Ne) to inhaled (Ni) particles per breath according to the following equation:

$$\frac{N_e}{N_i} = \frac{\int_{(te)} \dot{N}\, dt}{\int_{(ti)} \dot{N}\, dt}$$

where $\dot{N}$ is the corresponding counting rate (particle stream) during inhalation (ti) and exhalation (te).

The following table is a compilation of the different factors by which several gases differ from air in their Rayleigh scattering. For some of these gases, as for example He, Ne, Kr and Xe, the concentration measurement in the breathing air can be made with the aid of the photometer according to the invention.

| | Air | He | Ne | $H_2$ | $H_2O$ | Ar | Kr | $CO_2$ | Xe |
|---|---|---|---|---|---|---|---|---|---|
| Radio | 1 | 0.014 | 0.13 | 0.25 | 0.75 | 0.98 | 2.14 | 2.38 | 5.8 |

Figure 1:
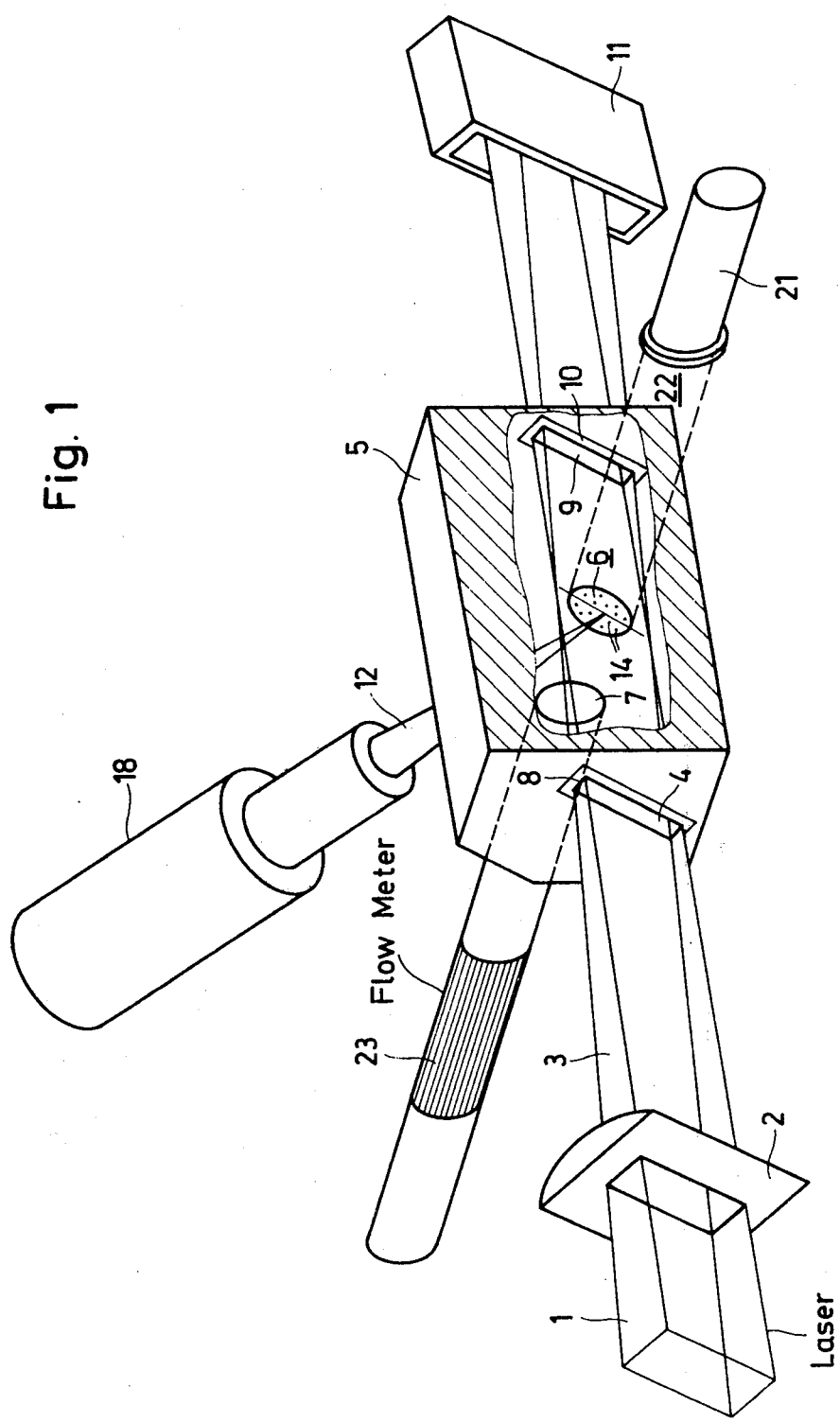
FIG. 1 is a schematic perspective view of the preferred embodiment of an apparatus according to the invention.
Figure 2:
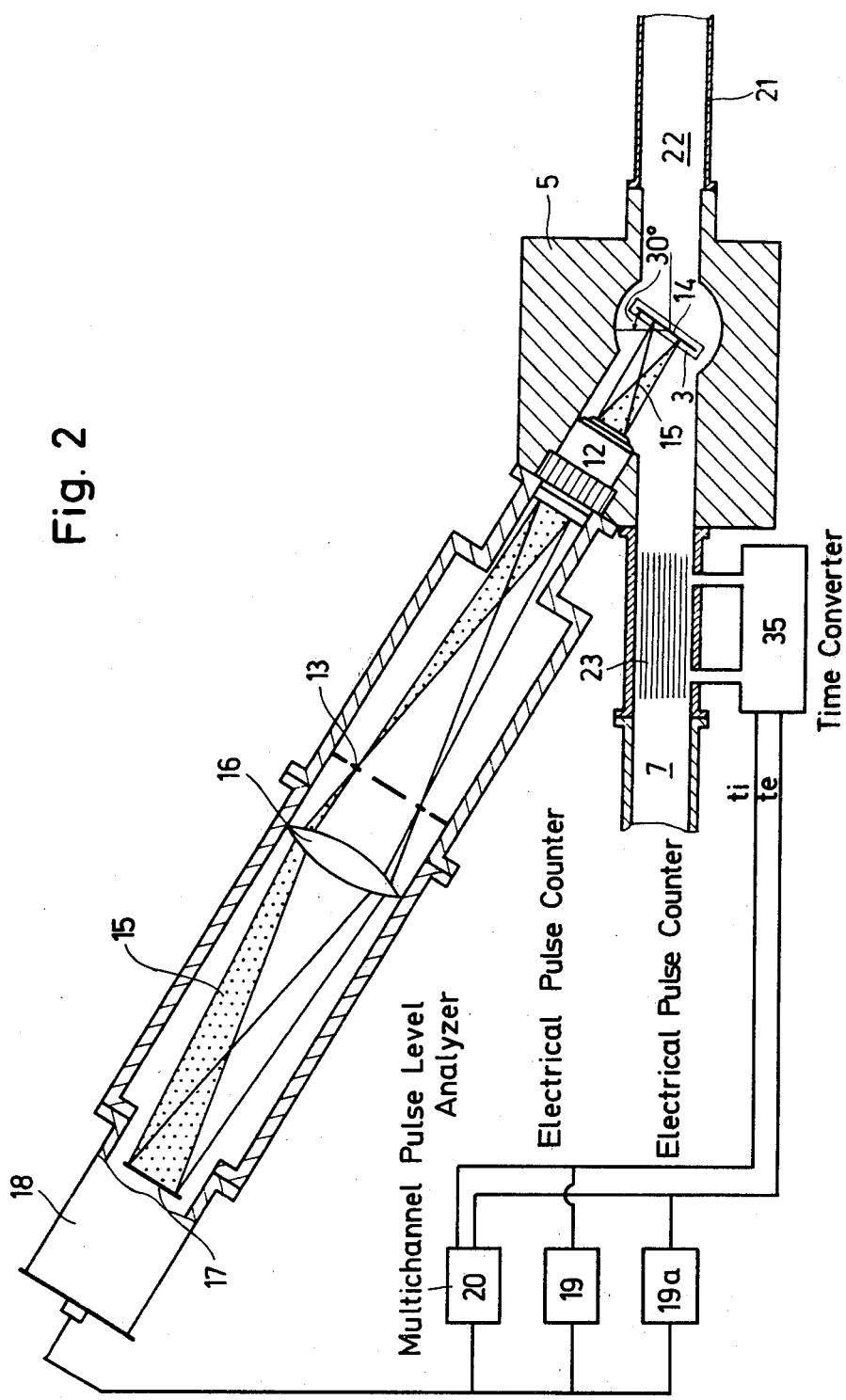
FIG. 2 is a schematic cross-sectional view of a portion of the apparatus of FIG. 1.

Turning now to the figures, a significant advance in the solution of the prior art problem mentioned above is accomplished by the present invention using the illustrated optical and mechanical structure. As shown in FIG. 1, the parallel beam of an Ar ion laser 1, of approximately 3 Watt, is converted with the aid of cylindrical lenses 2 into a narrow band of light 3 and is introduced in this shape into a slit-shaped element 4 of a housing 5 so that the point 6 of the greatest constriction of the band of light 3 (thickness: 80μ; width 15 mm) lies in the center of an aerosol or inhalation/exhalation channel 7 which likewise passes through the housing 5 and is oriented transverse to the channel 4. Preferably, as shown in FIG. 2, the cross-sectional plane of the channel 7 forms an angle of 30° with the plane of the band of light 3. The position of the objective 12 of the observing microscope relative to the band of light 3 and to the channel 7 is shown schematically in FIG. 1. The inlet of the slit-shaped channel 4 is closed off by means of a glass pane 8. After the band of light 3 has passed through the channel 7, it exits the housing 5 through a further opening or orifice 9 having a sealing pane or flange 10, and is absorbed in a light trap 11. The channel 7 is also provided with an orifice 21, which is engaged by the test patient to produce the inhalation of exhalation streams 22 in the channel 7, as well as a flow meter 23.

As best shown in FIG. 2, a microscope objective 12 is attached to the housing 5 so that the plane of the band of light 3 within the aerosol channel 7 is simultaneously the object plane of the microscope objective 12 which reproduces any particles 14 present in its objective plane in the plane of a field of view aperture 13. Due to the fact that the object plane of the microscope objective 12 and the plane of the light band 3 coincide, only those illuminated particles 14 in this common plane are excited into light scattering which can be sharply reproduced in the plane of the field of view aperture 13. This sharp image again assures that the scattered light signals of identical particles 14 are converted by the observation beam path 15 into identically sized measuring signals. In the case of an unsharp image, the height of the scattered light pulses does not depend only on the size of the particles 14 but also on their position in the field of view and consequently particle counting with simultaneous size analysis cannot be performed due to the poor resolution. The size of the field of view aperture 13 is dimensioned in such a way that a representative portion of the cross section of the aerosol channel 7 (about 40%) can be observed. A field lens 16 within the observation beam path 15 reproduces the exit opening of the microscope objective 12 on the cathode surface 17 of a photomultiplier 18 which converts the scattered light signals to electrical pulses which, after being suitably amplified, are then fed to electronic counters 19, 19a and a multichannel pulse level analyzer 20.

A flow meter 23 installed in the aerosol channel 7 indicates the direction of the flow 22 i.e. inhalation or exhalation. The electronic circuit 35 converts the direction of the flow into the time ti for inhalation and te for exhalation. The signal ti controls the electrical pulse counter 19 and the signal te controls the electrical pulse counter 19a. Both signals ti and te control the analyzer 20 and both counters 19, 19 in such a way that the measured signals from inhalation and exhalation are stored and processed separately. The flow meter 23 is a Fleisch-pneumotachograph with a pressure transducer EMT 32 produced by ELEMA-SCHÖANDER, Stockholm.

The digital counting method according to the invention can be performed as long as only one particle 14 on the average appears at a time in the field of view of the objective 12, which is assured for such an arrangement only for particle concentrations $C < 5^7/cm^3$. For particle concentrations $C > 10^{27}/cm^3$ and when measuring the Rayleigh scattering of gases, the photomultiplier 18 furnishes a continuous photocurrent instead of individual current pulses to be recorded by a graph (not shown) during inhalation and exhalation and which constitutes an analog measure for the concentration of the aerosol or a certain gas in the breathing air.

Figure 3:
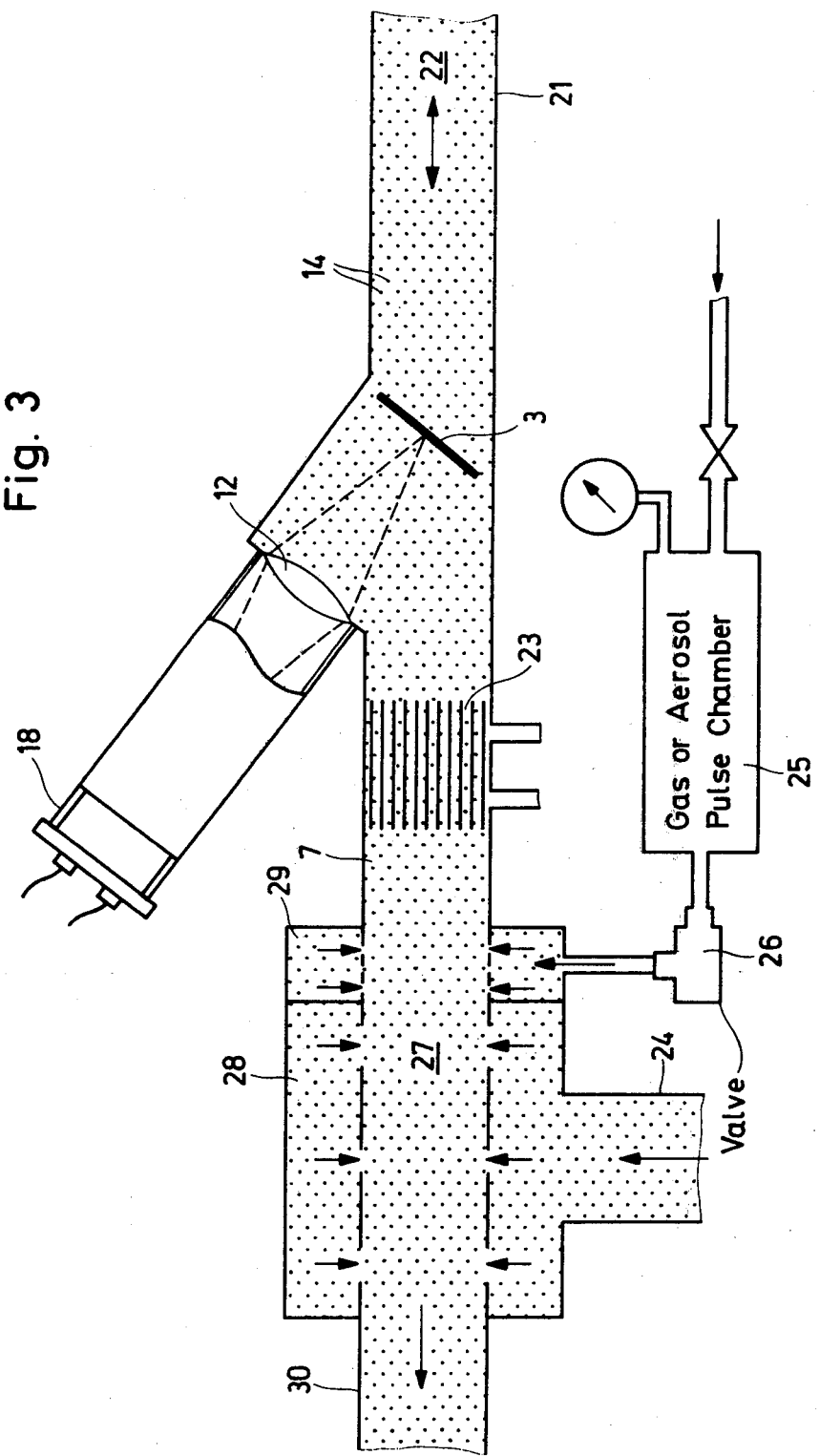
FIG. 3 is a schematic cross-sectional view of the inhaling and exhaling stream portion of the apparatus according to the invention.

In order to be able to mix a defined pulse of an aerosol or an inert gas into the inhaled air for an examination of the operating condition of the lungs of the test patient, a structure is provided which is shown schematically in FIG. 3. The main channel 7 for the breathing air 27 to be inhaled and exhaled by the test patient via the orifice 21, now receives pure air through a side channel 24 and openings in an annular chamber 28. A pulse chamber 25, of a volume of, for example, 150 cm³, is filled under pressure (0.5 to 1.5 bar) with an aerosol or with an inert gas. In a given phase during inhalation, a magnetic valve 26 is suddenly opened so that the contents of the pulse chamber 25 expand and are mixed, in the form of a pulse into the breathing air in the main channel 27 via opening in a further annular chamber 29. The spent breathing air in the stream 22 escapes through channel 30.

Figure 4:
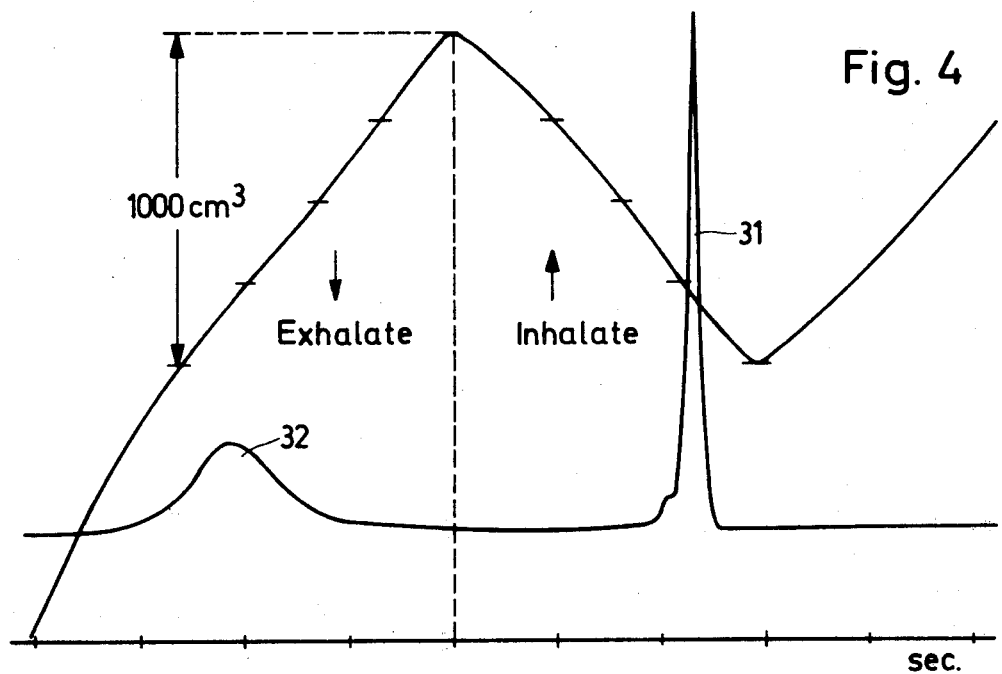
FIG. 4 is a curve showing the measurement of an aerosol pulse in the inhaled and exhaled air stream of a test patient.

FIG. 4 shows such an aerosol pulse 31 (particle diameter 0.5μ) in the inhaled air of a test patient and its subsequent deformation 32 in the exhaled air. This deformation provides information to the medical specialist about the operating condition of the respiratory tract of the test patient.

Figure 5:
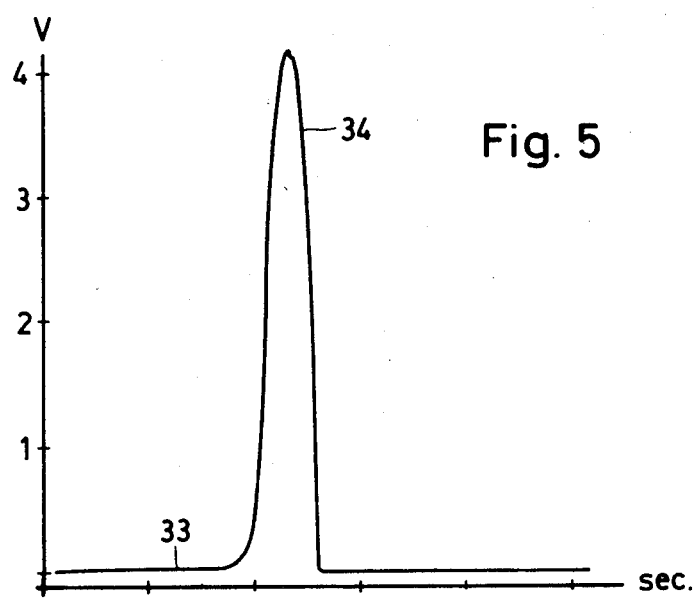
FIG. 5 shows the recorded curve for the Rayleigh scattering of air interrupted by a sudden pulse of carbon dioxide.

FIG. 5 shows the recorded curve 33 for the Rayleigh scattering of air which has been interrupted by the sudden pulse 34 of $CO_2$ gas. From the amplitude, of about 4 volts, of the pulse 34, the sensitivity with which the photometer arrangement reacts to the various gases can be seen.

It is to be understood that the above description of the present invention is susceptible to various modifications, changes and adaptations, and the same are intended to be comprehended within the meaning and range of equivalents of the appended claims.

What is claimed is:

1. In a method for determining the deposition of particles in the respiratory tract or for checking the operating function of the respiratory tract of a test patient including injecting a pulse of a gas or aerosol into a stream of air to be inhaled by a test patient and obtaining a measuring signal in each of the inhaled and exhaled streams of the test patient; the improvement comprising: directly conducting the main stream of the inhaled and of the exhaled air through a band of light; placing the region of the intersection of the band of light with at least part of the inhaled and exhaled streams in the object plane of an optical image system of a light detecting device; and detecting the light radiation produced in said object plane by the inhaled and the exhaled streams to provide said measuring signal.

2. The method defined in claim 1 wherein: a pulse of aerosol is injected; and said step of detecting includes counting the individual light pulses generated by the individual aerosol particles in the inhaled and exhaled streams to obtain the ratio of exhaled to inhaled numbers of particles.

3. The method defined in claim 1 wherein said step of detecting includes measuring the scattered radiation emanating from the gases and aerosol in the inhaled and exhaled streams to obtain the concentration profiles of the constituents of the inhaled and exhaled streams.

4. The method defined in claim 1, 2 or 3 wherein said step of detecting includes detecting the scattered light radiation produced in the object plane of the optical image system in the image plane of the optical image system.

5. The method defined in claim 2 wherein the concentration of aerosol particles in the inhaled and exhaled streams is less than 10 particles per cubic centimeters.

6. The method defined in claim 1 wherein the plane of said band of light is transverse to the direction of flow of said stream of inhaled and exhaled air.

7. Apparatus for determining the deposition of particles in the respiratory tract or for checking the operating function of the respiratory tract of a test patient by measuring light radiation from gases or aerosols in the inhaled and exhaled air streams of the test patient comprising in combination: a housing; channel means for conducting a stream of inhaled or exhaled air through said housing, said means having mouth piece at one end thereof for the inhaled and exhaled air of the test patient and a flow meter for the inhaled and exhaled air at the other end; means for conducting a narrow band of light through said housing in a direction transverse to the direction of said channel means and intersecting same within said housing; and a light measuring means including an optical observation system, said optical observation system being mounted on said housing such that its object plane coincides with the plane of intersection of said band of light and said channel means.

8. The apparatus defined in claim 7 wherein said flow meter includes means for determining the direction of the stream of inhaled and exhaled air in said channel means.

9. The apparatus defined in claim 7 further comprising means, connected to said channel means so that said housing is between same and said mouth piece, for selectively injecting a pulse of a gas or aerosol into the air stream to be inhaled by the test patient.

10. The apparatus defined in claim 9 wherein said means for selectively injecting includes: a pulse chamber filled under pressure with the gas or aerosol, a normally closed valve connected between said pulse chamber and said channel means, and means for opening said valve at a desired time, whereby opening of said valve at a desired time during the inhalation of the air stream by the test patient will cause the gas or aerosol in said test chamber to expand and enter said channel means for inhalation by the test patient.

11. The apparatus defined in claim 7 wherein the plane of said narrow band of light is transverse to said direction of said channel means.

12. Tha apparatus defined in claim 11 wherein said plane of said narrow band of light forms an angle of 30° with the cross-sectional plane of said channel means.

13. The apparatus defined in claim 7 or 11 wherein said means for conducting includes a laser and lense means for converting the output of said laser to a narrow band of light whose point of greatest constriction lies in said plane of intersection.

14. Ths apparatus defined in claim 7 wherein said light measuring means includes first and second pulse counters for storing the number of detected pulses in the inhaled and exhaled streams respectively.

* * * * *